(12) United States Patent
Nagabhatla et al.

(10) Patent No.: US 8,349,754 B2
(45) Date of Patent: Jan. 8, 2013

(54) MODIFIED ZEOLITE CATALYST USEFUL FOR THE CONVERSION OF PARAFFINS, OLEFINS AND AROMATICS IN A MIXED FEEDSTOCK INTO ISOPARAFFINS AND A PROCESS THEREOF

(75) Inventors: Viswanadham Nagabhatla, Dehradun (IN); Raviraj Kamble, Dehradun (IN); Amit Sharma, Dehradun (IN); Jagdish Kumar, Dehradun (IN); Bhagwan Singh Negi, Dehradun (IN); Murali Dhar Gudimella, Dehradun (IN); Madhukar Onkarnath Garg, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 659 days.

(21) Appl. No.: 12/399,717

(22) Filed: Mar. 6, 2009

(65) Prior Publication Data
US 2009/0292154 A1 Nov. 26, 2009

(30) Foreign Application Priority Data

Mar. 26, 2008 (IN) .............................. 776/DEL/2008

(51) Int. Cl.
*B01J 29/06* (2006.01)
(52) U.S. Cl. ................ 502/64; 502/60; 502/63; 502/66; 502/69; 502/71; 502/74; 502/78
(58) Field of Classification Search .................... 502/60, 502/63, 64, 66, 69, 71, 74, 78
See application file for complete search history.

(56) References Cited

U.S. PATENT DOCUMENTS

| | | | |
|---|---|---|---|
| 3,480,539 A | 11/1969 | Voorhies, Jr. et al. | ... 208/111.15 |
| 3,507,931 A | 4/1970 | Morris et al. | ................. 585/739 |
| 4,018,711 A | 4/1977 | Bertolacini | ..................... 502/66 |
| 4,400,576 A | 8/1983 | den Otter | ...................... 585/739 |
| 4,485,005 A | 11/1984 | O'Hara | ....................... 208/111.3 |
| 4,610,856 A * | 9/1986 | Skeels et al. | ................... 423/715 |
| 4,734,539 A | 3/1988 | Lawlor et al. | ................. 585/739 |
| 4,735,929 A * | 4/1988 | Bakas et al. | ..................... 502/66 |
| 4,962,269 A | 10/1990 | La Pierre et al. | ............. 585/739 |
| 5,057,472 A | 10/1991 | Herzengerg et al. | ............ 502/66 |
| 5,238,677 A | 8/1993 | Apelian et al. | ................. 423/714 |
| 5,770,047 A | 6/1998 | Salazal et al. | ............. 208/254 R |
| 6,964,935 B2 | 11/2005 | Harris et al. | .................... 502/78 |
| 2006/0063956 A1 * | 3/2006 | Kalnes et al. | ................. 585/639 |

\* cited by examiner

*Primary Examiner* — Elizabeth Wood
(74) *Attorney, Agent, or Firm* — Fulbright & Jaworski L.L.P.

(57) ABSTRACT

The invention relates to a modified zeolite catalyst, useful for the conversion of paraffins, olefins and aromatics in a mixed feedstock such as FCC gasoline that contain high content of olefin, aromatic and n-paraffin into isoparaffins. The invention further relates to the use of such a catalyst, for example but not limited to, in a process for the conversion of paraffins, olefins and aromatics in a mixed feedstock into the product having high amount of branched paraffins with decreased aromatics and olefins, a useful gasoline blend, with negligible production of lighter gases.

3 Claims, No Drawings

MODIFIED ZEOLITE CATALYST USEFUL FOR THE CONVERSION OF PARAFFINS, OLEFINS AND AROMATICS IN A MIXED FEEDSTOCK INTO ISOPARAFFINS AND A PROCESS THEREOF

BACKGROUND OF THE INVENTION

1. Field of the Invention

The present invention relates to a modified zeolite catalyst useful for the conversion of paraffins, olefins and aromatics in a mixed feedstock into isoparaffins. More particularly, the present invention relates to a porosity and acidity modified zeolite comprising one or two noble metals. The present invention also relates to a process for the conversion of paraffins, olefins and aromatics in a mixed feedstock into isoparaffins. The utility of the process is for upgrading the octane number of a industrial feedstock such as desulfurized FCC gasoline through conversion of most of the olefins and aromatics present in it into environment friendly branched paraffins, using porosity improved, noble metal containing zeolite based catalyst, so as to meet the quality requirement of fuel to use as gasoline blending stock.

2. Description of Related Art

Environmental concern and restriction on fuel quality especially on the restriction on the amount of sulfur, aromatic and olefins in FCC gasoline demands novel catalyst and process for hydrocarbon conversion. The octane loss occurred during traditional sulfur removal process also demands hydrocarbon conversion process for octane boosting in an eco-friendly way. The present invention relates to a process for hydroconversion of feedstocks, especially FCC gasoline, to a catalyst for use in hydro conversion process with a feedstock having high amount of paraffins, olefins and aromatics to produce branched paraffin and to a process provides such catalyst.

Reference may be made to the U.S. Pat. No. 4,734,539 to Lawlor et al, wherein a process for the isomerization of paraffins is disclosed. The drawback of the process is that the catalyst has one dimensional pore system that leads to rapid deactivation by coke as well.

References may be made to U.S. Pat. No. 4,962,269 to La pierre et al, wherein a process for isomerization of paraffins using zeolite catalyst was described. The drawback of the process is the formation of considerable amount of aromatics that are undesirable for the production of green gasoline. On the other hand, the present invention deals with the conversion of aromatics into iso-paraffins.

Reference may be made to U.S. Pat. No. 5,770,047 to Salazal et al, wherein a process for removal of sulfur and nitrogen from the heavy naphtha was described. The process also describes a GaCr/ZSM-5 catalyst for the isomerization of paraffin. The drawback of the process is the formation of considerable amount of undesirable gases (C1-C4 up to 25%).

Reference may be made to the U.S. Pat. No. 5,057,472, wherein a process for dealumination of zeolites, especially by adding ammonium nitrate and nitric acid for obtaining effective isomerization catalyst that can isomerizes n-paraffins to isoparaffins. However, the process does not cover the procedure for obtaining the zeolite with improved surface area, porosity or acidity and improved Pt dispersion that are essential for conversion aromatics, olefins and naphthenes into isoparaffins. The patent also does not mention its effectiveness for conversion of aromatics viz. especially for the conversion of benzene so as to meet the requirement of gasoline specifications.

Reference may be made to the U.S. Pat. Nos. 5,238,677 and 4,485,005, wherein processes for dealumination of mordenite using an acid such as dicarboxylic acid and steaming have been described. The catalysts are tested for their alpha activity related to its cracking ability and for the cracking of long chain vacuum gas oil. However, the processes do not discuss the improvement in catalytic properties such as porosity and acidity, and its catalytic activity towards the conversion of olefins, naphthenes and aromatics.

Reference may be made to the U.S. Pat. No. 6,964,935, wherein the patent describes a process for alkylation of benzene with long chain olefins to produce alkyl aromatics. The process does not cover the conversion of short chain paraffins, olefins, naphthenes and aromatics into gasoline range isoparaffins. Nitric acid was used for peptization of extrudates but not for dealumination purpose.

Reference may be made to the U.S. Pat. Nos. 3,507,931 (MORRIS), 4,018,711 (BERTOLACINI), 4,400,576 (SHELL), 3,480,539 (ESSO), wherein a process for the isomerization of paraffins was described using a zeolite treated with steam and acids at severe conditions prior to the contact with feed. But, the processes limits to the conversion of paraffins into isoparaffins. Whereas, the present invention deals with the conversion of aromatics, olefins and naphthenes present in the feed into iso-paraffins. Based on the prior art details and drawbacks thereof, the present work is intend to provide a process for the reformulation of the FCC gasoline, where, most of the olefins and aromatics present in the feed have been converted into branched paraffins using a porosity modified, acidity modified zeolite supported noble metal based catalyst.

SUMMARY OF THE INVENTION

The main object of the invention is to provide a modified zeolite catalyst, useful for the conversion of paraffins, olefins and aromatics in a mixed feedstock such as FCC gasoline that contain high content of olefin, aromatic and n-paraffin into isoparaffins.

Yet another objective is to provide a process for the conversion of paraffins, olefins and aromatics in a mixed feedstock into the product having high amount of branched paraffins with decreased aromatics and olefins, a useful gasoline blend, with negligible production of lighter gases.

Yet another object of the present invention is to provide a process for the conversion of benzene in the hydrocarbon feedstock by saturation and ring opening to form iso-paraffins.

Yet another object of the invention is to provide a catalyst for improving the octane number of the industrial FCC gasoline to at least 10-15 units of RON.

Yet another object of the invention is to provide such a hydro conversion catalyst, which provides significant level of isomerization product.

Still another object of the invention is to provide a process for preparing a catalyst with improved properties such as pore volume, surface area and strong acidity, suitable for the improved production of branched paraffins in accordance with the invention.

Some advantages of the present invention are:
  A porosity and acidity improved catalyst that can enhance the formation of bulky iso-paraffins having high octane number
  The catalytic process can convert undesired aromatics and olefins present in the feedstock into environment friendly isoparaffins.

The catalytic process reduces aromatics and olefins in the feedstock without any octane loss.

The process can be used for the improvement of research octane number (RON) of the feedstocks, at least by 8 units.

Accordingly the present invention provides a modified zeolite catalyst with improved acidity and porosity, useful for the conversion of paraffins, olefins and aromatics in a mixed feedstock into isoparaffins, said catalyst comprises noble metal incorporated pentasil zeolite based catalyst, the composition comprised of:

| | |
|---|---|
| Zeolite: | in the range of 59-60 wt %; |
| Pseudo extrude: | in the range of 39-40 wt %; |
| Pt: | in the range of 0.1-1.0 wt %; |
| Pd: | in the range of 0-1.0 wt %; | and said catalyst has the following characteristics:

| | |
|---|---|
| Si/Al | in the range of 16-80 |
| BET surface area (m$^2$/g) | in the range of 200-350 |
| Micropore area (m$^2$/g) | in the range of 155-250 |
| External pore area (m$^2$/g) | in the range of 90-135 |
| Pore volume (cc/g) | in the range of 0.30-0.50 |
| Acidity (m · mol/g · catal) | in the range of 1.40-1.60 |
| Strong (>120 kJ/mol) | in the range of 0.40-0.60 |
| Medium(120-80 kJ/mol) | in the range of 0.45-0.50 |
| Weak(<80 kJ/mol) | in the range of 0.40-0.60 |
| Pt dispersion (%) | in the range of 60-80 |

In an embodiment of the present invention the modified catalyst has the following composition:

| | |
|---|---|
| Zeolite: | 59.8 wt % |
| Pseudo extrude: | 39.7 wt % |
| Pt: | 0.3 wt % |
| Pd: | 0.2 wt % |

In yet another embodiment, the modified catalyst has the following characteristics:

| | |
|---|---|
| Si/Al | 39 |
| BET surface area (m$^2$/g) | 347 |
| Micropore area (m$^2$/g) | 248 |
| External pore area (m$^2$/g) | 99 |
| Pore volume (cc/g) | 0.4734 |
| Acidity (m · mol/g · catal) | 1.48 |
| Strong (>120 kJ/mol) | 0.58 |
| Medium(120-80 kJ/mol) | 0.49 |
| Weak(<80 kJ/mol) | 0.41 |
| Pt dispersion (%) | 78 |

In yet another embodiment the modified zeolite catalyst is useful for the conversion of paraffins, olefins and aromatics in a mixed feedstock into isoparaffins.

The present invention further provides a process for the preparation of modified zeolite catalyst useful for the conversion of paraffins, olefins and aromatics in a mixed feedstock into isoparaffins and the said process comprising the steps of:

treating the zeolite mordenite with steam, at a temperature of 300-700° C., for 2-6 hrs in a shallow bed reactor for dealumination, followed by washing with 0.01-2N acid solution, at 100-110° C. for 2-6 hrs and further washing with deionized water to remove the extra-framework debris of the zeolite and the nitrate ions;

shaping the above said zeolite catalyst obtained in step (a) by mixing it with an inert alumina binder, preferably pseudo bemire, with zeolite to binder ratio in the range of 3:1 to 3:2.5 by weight, followed by adding 2-3 vol % glacial acetic acid and allowing the above said mixture for peptization to obtain a homogeneous paste, followed by extrusion, drying at 20-30° C., for 10-12 h and calcinations at 500° C. for 2-6 hrs; and loading the above said extruded catalyst obtained in step (b) with the noble metal ions by incipient wet impregnation method (IWI) using Pt tetrammonium chloride and or Pd chloride as a source of salts, followed by calcination at 500-600° C. for 4-6 hrs to obtain the desired modified catalyst.

In yet another embodiment, the steaming temperature used in step (a) is preferably in the range of 350-650° C. for a period of 1-4 hr.

In yet another embodiment, the ratio of the volume of the support to the acid solution taken in step (a) is preferably equal to about 50:50.

In yet another embodiment, the acid used in acid solution is selected from the group consisting of hydrochloric acid, sulfuric acid, nitric acid, oxalic acid and mixture of two or more acids.

In yet another embodiment, the noble metals used in step (c) is Pt or Pd or a combination thereof.

In yet another embodiment, the amount of metal used is in the range of 0.1 to 1 wt % each.

In yet another embodiment, the surface area and pore volume of the catalyst material obtained in step (c) is increased by 10-15% and 20-30% respectively after the treatment.

In yet another embodiment, the acidity of the catalyst obtained is increased to 10-30% after treatment.

The present invention further provides a process for the conversion of paraffins, olefins and aromatics in a mixed feedstock into isoparaffins which comprises feeding FCC gasoline having paraffin, iso-paraffin, olefin, naphthenes and aromatics into the fixed bed down flow reactor containing a modified zeolite catalyst comprising noble metals in the range of 0.1 to 1 wt %, under hydrogen flow, at a temperature in the range of 225-375° C., at a pressure in the range of 5-35 bar, at a space velocity of 1-6 h$^{-1}$, followed by cooling of the gaseous product at the reactor tail to obtain the desired product.

In yet another embodiment, the modified catalyst used has a composition of:

| | |
|---|---|
| Zeolite: | 59.8 wt % |
| Pseudo extrude: | 39.7 wt % |
| Pt: | 0.3 wt % |
| Pd: | 0.2 wt % |

In yet another embodiment, the modified catalyst has the following characteristics:

| | |
|---|---|
| Si/Al | 39 |
| BET surface area (m$^2$/g) | 347 |
| Micropore area (m$^2$/g) | 248 |
| External pore area (m$^2$/g) | 99 |
| Pore volume (cc/g) | 0.4734 |
| Acidity (m · mol/g · catal) | 1.48 |
| Strong (>120 kJ/mol) | 0.58 |

-continued

| | |
|---|---|
| Medium (120-80 kJ/mol) | 0.49 |
| Weak (<80 kJ/mol) | 0.41 |
| Pt dispersion (%) | 78 |

In yet another embodiment, the feed stock used contains about 80% olefins and about 60% aromatics.

In yet another embodiment, the feed stock used has an octane number of 69 RON.

In yet another embodiment, the octane number of the gasoline obtained is increased by 20-40% as compared to initial RON number.

In yet another embodiment, the hydro conversion of the feedstock resulted in an increase in octane number in the range of 10 to 15 units of RON.

In still another embodiment, the branched paraffins obtained in the final product is increased by 30-70% as compared to isoparaffins present in the feedstock.

DETAILED DESCRIPTION OF THE INVENTION

In accordance with invention, a catalyst system is described which comprises a porosity and acidity modified zeolite and a catalytically active phase supported on the support medium and comprising one or two noble metals.

In an embodiment of the present invention, a catalyst system, particularly a hydrocarbon conversion catalyst was described for use in the conversion of FCC gasoline and the like so as to convert the olefins and aromatics into branched paraffins and providing gasoline or gasoline additives having improved RON/MON values. In accordance with the invention, the catalyst can also convert the n-paraffins and naphthenes into branched paraffins and prevent the undesirable aromatic production.

The catalyst system consisting of a silicious molecular sieve support and an inert binder material, a catalytically active phase consisting of one or two noble metals, supported or incorporated on the medium, was described for the reformulation of FCC gasoline. The matrix used was aluminum, preferably in the form of monohydroxide, and active metal phase is from VIII group of the periodic table, preferably Pt. The matrix further includes or supports additional metal to change the electronic properties of the first metal. The second metal includes Ni, Co, Pd most preferably Pd. Of the foregoing metals, the total ratio in the final catalyst by weight of Pt to Pd is preferably 0.5 to 5, the total ratio by weight of metal to support is 0.2 to 1 wt %. This combination of metals provides the catalyst system with improved catalytic properties discussed in the examples below.

The support medium is preferably a hydrothermally stable porous crystalline silicious molecular sieve material, preferably a zeolite of Pentasil type. In accordance with the most preferred embodiment of the invention, the support material underwent the modification treatment in a hollow reactor at 300° C. to 700° C. in presence of steam followed by washings with acid such as HCl, $HNO_3$, $H_2SO_4$, preferably $HNO_3$ with acid concentrations of 0.01 to 1N. The treatment caused considerable improvement in porosity of the support as discussed in the example below. The support medium preferably has a surface area between 200 $m^2$/gm to 350 $m^2$/gm, pore volume of 0.30 to 0.45 cc/g and Si/Al atomic ratio of 16 to 80 preferably around 40.

The catalytically active phase which supported on the support medium preferably includes at least two catalytically active metals, preferably Pt and the other can be Ni, Co or Pd. Pt and Pd are each present as oxide in the final catalyst in an amount of between 0.01% to about 5% by weight of the catalyst by any means known in the art such as impregnation, ion-exchange, addition of metal to the molecular sieve material during its hydrothermal synthesis and the like. Impregnation is preferably carried out with a salt of the metal in aqueous medium preferably salts includes $Pt(NH_3)_4Cl_2$, $Pd(NO_3)_2.H_2O$. Each impregnation is preferably followed by a drying step carried out at a temperature range of between 80° C. to 150° C. preferably about 110° C. under flow of air for a period of 3 to 6 hours. Further, the total ratio by weight in the catalyst of Pt to Pd is preferably between 1 to 10. The catalyst elements are then calcined in accordance with invention so as to provide the final catalyst. In accordance with invention, calcination is carried at temperature 600° C. for a period of about 6 hours under flow of air.

The final catalyst exhibits a ratio of Si/M, where M is defined as group IIIA metal, of between about 15 to 60. The final catalyst preferably has a Si/M of about 16-80, particle diameter of between 0.5 mm to 3 mm, a surface area of about 200 $m^2$/gm to 350 $m^2$/gm, a pore volume of between 0.3 to 0.45 cc/g.

Still further, a process is also disclosed for upgrading olefins rich, aromatic rich FCC gasoline which process comprises the steps of providing the FCC gasoline having an initial olefins content, aromatic content and initial octane number, and contacting said feedstock with a hydroconversion catalyst system under a hydrogen atmosphere, temperature and pressure so as to provide a final product having a final olefins and aromatic content less than that of initial FCC gasoline, and having a final octane number which is 5-15 RON units greater than said initial octane number of the feedstock, and wherein the final product has an increased branched paraffin component with effect to said feedstock.

The process as set forth above provides the catalyst of invention, which yields considerable amount of branched paraffins and potential for octane boosting of FCC gasoline.

The catalyst is preferably loaded in a fixed bed reactor and contacted with the feed stock under process condition effective to provide the desired reaction typically includes the hydrogen pressure 5 to 35 bar, temperature between 225 to 375° C., a space velocity between 1 to 6 $h^{-1}$. In accordance with the present invention, a process is provided for reducing olefins and aromatics in the FCC gasoline and for the produced branched paraffin with improved octane number.

The final product obtained after contacting the feed stock with the catalyst system of the invention is characterized by an upgraded product having improved characteristics. The final product exhibits considerable improvement in the concentration of hydrocarbon types; about 70 to 140% increase in branched paraffins, 30-80% decrease in olefins and 20-60% decrease in aromatics, when compared to those in feed stock. The final product exhibited significant increase in the octane number; 20 to 40% increase in RON.

In an embodiment of the present invention, a catalyst system, particularly a hydrocarbon conversion catalyst was described for use in the conversion of FCC gasoline and the like so as to convert the olefins and aromatics into branched paraffins and providing gasoline or gasoline additives having improved RON/MON values. In accordance with the invention, the catalyst can also convert the n-paraffins and naphthenes into branched paraffins and prevent the undesirable aromatic production.

The catalyst according to the invention exhibits improved octane number by converting olefins and aromatics into branched paraffin as shown in the examples to follow.

EXAMPLES

The following examples are given by the way of illustration and therefore should not be construed to limit the scope of the invention.

Example 1

This example illustrates the preparation of two catalysts of the invention. The chemical composition of the two catalysts is set below in Table 1. The catalysts were prepared as follows. H-mordenite zeolites was obtained as support (support-A). Another H-mordenite zeolites was obtained by treating the "support A" in a shallow bed reactor at 500° C. for 3 hours under steam, followed by washing with 2N $HNO_3$ and distilled water. The support obtained after the treatment is called "support B." Both the supports are used for making two extrudates, where the support is mixed with pseudo boehmite alumina, added required amount of 3 volume % glacial acetic acid, to obtain a homogeneous paste, which was extruded and dried. The extrudates obtained are called extrudate A and extrudate B, respectively. The extruded catalyst elements were then impregnated with aqueous solution of $Pt(NH_3)_4Cl_2$, $Pd(NO_3)_2 \cdot H_2O$. The impregnated solid was then dried and calcined so as to provide catalyst described in Table 2.

TABLE 1

Chemical components of the catalyst

| Catalyst | Catalyst A | Catalyst B |
| --- | --- | --- |
| Zeolite (wt %) | 59.8 | 59.8 |
| Pseudo extudate (wt %) | 39.9 | 39.7 |
| Pt (wt %) | 0.3 | 0.3 |
| Pd (wt %) | 0.0 | 0.2 |

This example illustrates the importance of steaming and acid washing on the properties of the zeolites support. Catalyst B is the most preferred catalyst of the invention and has exhibited improved properties such as enhanced porosity and surface area (about 33% increase in pore volume and 14% increase in surface area). The support also exhibits improved dispersion of the Pt on the support (Table 2).

TABLE 2

Improvement in properties of the mordenite.

| | Catalyst A | Catalyst B |
| --- | --- | --- |
| Si/Al | 18 | 39 |
| BET surface area (m²/g) | 292 | 347 |
| Micropore area (m²/g) | 158.5 | 248 |
| External pore area (m²/g) | 133.5 | 99 |
| Pore volume (cc/g) | 0.3462 | 0.4734 |
| Acidity (m · mol/g · catal) | 1.60 | 1.48 |
| Strong (>120 kJ/mol) | 0.42 | 0.58 |
| Medium(120-80 kJ/mol) | 0.50 | 0.49 |
| Weak(<80 kJ/mol) | 0.62 | 0.41 |
| Pt dispersion (%) | 62 | 78 |

Example 2

This example illustrates the isomerization activity of the catalyst A and B. The catalysts were used in hydroisomerization of n-hexane at reaction temperature 310° C., pressure 20 bar, $H_2/n-C_6=2.1$ WHSV=2. As shown in table 3, catalyst B provided higher n-hexane conversion and isomer yields. As can be seen, the selectivity towards bulky di-branch isomer 22 DHD and 23 DHB significantly high on the catalyst B. The di/mono branched isomer ratio indicating the formation of bulky products increased from 0.29 to 0.43 (compared to catalyst A). This is an ideal situation for the octane boosting of the product, as branching improves the RON of the feed.

TABLE 3

Ability of catalysts in n-hexane conversion

| Samples | Catalyst A | Catalyst B |
| --- | --- | --- |
| n-hexane conversion (wt %) | 20.0 | 36.9 |
| iso-hexane yield (wt %) | 19.8 | 36.5 |
| Selectivities (wt % of the total isomer) | | |
| 2-methyl pentane | 48.9 | 43.6 |
| 3-methyl pentane | 28.8 | 26.6 |
| 2,2-dimethyl butane | 11.7 | 14.8 |
| 2,3-dimethyl butane | 10.6 | 15.0 |
| Di/mono ratio | 0.29 | 0.43 |

Example 3

Catalyst B of Example 2 was further used in the hydroisomerzation of FCC gasoline (60-FBP). As can be seen in Table 4, the feedstock exhibits the following characteristic, with high level of olefins and aromatics. The feedstock also contains the some amount of isomers.

TABLE 4

Feed properties and ASTM distillation

| Feed Properties | |
| --- | --- |
| Density at 15° C. | 0.7142 |
| Nitrogen | 5.5 |
| RVP (Kpa) | — |
| Bromine No. | 109.3 |
| MAV | 2.8 |
| Sulfur (ppm) by XRF | 20 |
| ASTM distillation | |
| IBP° C. | 23.9 |
| 5% vol | 45.6 |
| 10% vol | 51.5 |
| 20% vol | 55.8 |
| 30% vol | 60.6 |
| 40% vol | 67.7 |
| 50% vol | 75.4 |
| 60% vol | 86.4 |
| 70% vol | 99.0 |
| 80% vol | 113.0 |
| 90% vol | 127.7 |
| 95% vol | 135.5 |
| FBP° C. | 137.9 |
| Total recovery % vol | 98.6 |
| Residue % vol | 1.0 |

The data given in Table 5 illustrates the hydrocarbon types present in FCC gasoline and their conversion into reformulated product. This example illustrates the hydro-conversion of olefin, aromatic, paraffin found in the FCC gasoline over the catalyst A and catalyst B. The hydro-conversion reaction was conducted at similar conditions as mentioned in Example 2. As shown in Table 5, the product obtained exhibited improved isomer yields. In addition to this, the aromatics and olefin contents are decreased significantly.

A small amount of naphthenes are also formed. This example also illustrates that catalyst B is effective for the conversion of olefin and aromatics in FCC gasoline into isomers. About 80% of olefins and 60% of aromatics are converted to increase 140% of branched paraffins in the product.

The results suggest the mechanism of iso-paraffin formation from aromatics and olefins through saturation, ring opening and isomerization. The RON of the feed increased from 69 to 81.

TABLE 5

Catalyst ability in conversion of hydrocarbon types

| Hydrocarbon types | Feed | Product Catalyst A | Catalyst B |
|---|---|---|---|
| n-paraffins | 12.5 | 17.8 | 14.7 |
| Isoparaffins | 23.9 | 37.2 | 59.0 |
| Olefins | 15.9 | 9.7 | 2.5 |
| Naphthenes | 21.2 | 16.2 | 12.2 |
| Aromatics | 26.5 | 19.1 | 11.6 |
| Total | 100.0 | 100.0 | 100.0 |
| RON | 69 | 75.5 | 81.2 |

Example 4

This example illustrates the types of branched hydrocarbons formed during hydro-conversion of FCC gasoline. As can be seen from Table 6, a variety of branched paraffins are formed after the processing of the FCC gasoline. Catalyst B stands better as the amount of such branched paraffins formed is 35 wt % against 13.3 wt % over catalyst A. Almost three (3) times increase in isomer yield was observed on catalyst B and can be ascribed to the improved catalytic properties of catalyst after steaming and acid washings.

TABLE 6

Improvement in branched products

| Hydrocarbon | Catalyst A | Catalyst B |
|---|---|---|
| Iso-pentane | 1.2 | 1.9 |
| 2-methyl hexane | 2.3 | 4.6 |
| 2,3-dimethyl pentane | 0.5 | 1.1 |
| 3-methyl hexane | 2.2 | 4.4 |
| 3-ethyl pentane | 0.6 | 1.3 |
| 2,5-dimethyl hexane | 0.4 | 0.9 |
| 2,2,3-trimethyl hexane | 0.6 | 2.2 |
| 2-methyl heptane | 1.7 | 4.0 |
| 4-methyl heptane | 0.4 | 1.1 |
| 3-methyl heptane | 1.2 | 4.6 |
| 3-ethyl hexane | 0.3 | 3.5 |
| 4-methyl octane | 0.6 | 2.8 |
| 3-methyl octane | 1.1 | 2.7 |
| Total | 13.3 | 35.1 |

What is claimed is:

1. A modified zeolite catalyst with improved acidity and porosity, useful for the conversion of paraffins, olefins and aromatics in a mixed feedstock into isoparaffins, said catalyst comprising noble metal incorporated mordenite zeolite based catalyst comprising:

| | |
|---|---|
| Zeolite: | in the range of 59-60 wt %; |
| Pseudo extrude: | in the range of 39-40 wt %; |
| Pt: | in the range of 0.1-1.0 wt %; |
| Pd: | in the range of 0-1.0 wt %; | and said catalyst has the following characteristics:

| | |
|---|---|
| Si/Al | in the range of 16-80 |
| BET surface area ($m^2/g$) | in the range of 200-350 |
| Micropore area ($m^2/g$) | in the range of 155-250 |
| External pore area ($m^2/g$) | in the range of 90-135 |
| Pore volume (cc/g) | in the range of 0.30-0.50 |
| Acidity (m · mol/g · catal) | in the range of 1.40-1.60 |
| Strong (>120 kJ/mol) | in the range of 0.40-0.60 |
| Medium(120-80 kJ/mol) | in the range of 0.45-0.50 |
| Weak(<80 kJ/mol) | in the range of 0.40-0.60 |
| Pt dispersion (%) | in the range of 60-80. |

2. The modified catalyst of claim 1, further defined as comprising:

| | |
|---|---|
| Zeolite: | 59.8 wt % |
| Pseudo extrude: | 39.7 wt % |
| Pt: | 0.3 wt % |
| Pd: | 0.2 wt %. |

3. The modified catalyst of claim 1, wherein said catalyst has the following characteristics:

| | |
|---|---|
| Si/Al | 39 |
| BET surface area ($m^2/g$) | 347 |
| Micropore area ($m^2/g$) | 248 |
| External pore area ($m^2/g$) | 99 |
| Pore volume (cc/g) | 0.4734 |
| Acidity (m · mol/g · catal) | 1.48 |
| Strong (>120 kJ/mol) | 0.58 |
| Medium(120-80 kJ/mol) | 0.49 |
| Weak(<80 kJ/mol) | 0.41 |
| Pt dispersion (%) | 78. |

* * * * *